（12）United States Patent
Bays

(10) Patent No.: US 6,391,017 B2
(45) Date of Patent: May 21, 2002

(54) METHOD FOR PROTECTING SOFT TISSUE WHILE DRILLING INTO UNDERLYING BONE

(75) Inventor: F. Barry Bays, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 09/851,151

(22) Filed: May 9, 2001

Related U.S. Application Data

(62) Division of application No. 09/305,342, filed on Apr. 30, 1999, now Pat. No. 6,238,400.
(60) Provisional application No. 60/083,762, filed on May 1, 1998.

(51) Int. Cl.[7] ............................................. A61M 31/00
(52) U.S. Cl. ..................................................... 604/506
(58) Field of Search ................................. 604/500, 506, 604/508, 158, 164, 264, 268, 164.01, 59, 60, 27, 28; 606/79, 80, 96

(56) References Cited

U.S. PATENT DOCUMENTS

| | | | |
|---|---|---|---|
| 3,892,232 A | | 7/1975 | Neufel |
| 4,549,538 A | | 10/1985 | Schadrack, III et al. |
| 5,041,082 A | * | 8/1991 | Shiber .......................... 604/22 |
| 5,049,150 A | | 9/1991 | Cozad |
| 5,409,493 A | | 4/1995 | Greenberg |
| 5,855,579 A | | 1/1999 | James et al. |
| 5,895,389 A | | 4/1999 | Schenk et al. |
| 5,951,561 A | | 9/1999 | Pepper et al. |
| 5,976,105 A | | 11/1999 | Marcove et al. |
| 6,083,228 A | * | 7/2000 | Michelson ................... 606/79 |

OTHER PUBLICATIONS

Micro–France publication, 1 page, "E.N.T.—Basic Instruction Rhinology", 1993.

\* cited by examiner

*Primary Examiner*—Sharon Kennedy

(57) ABSTRACT

A method of protecting soft tissue while drilling into underlying bone includes the steps of making an incision in the soft tissue, inserting a protector sleeve into the incision to engage the bone, inserting a drill through the protector sleeve, and using the drill to drill into the bone with the protector sleeve protecting the soft tissue from the drill.

4 Claims, 11 Drawing Sheets

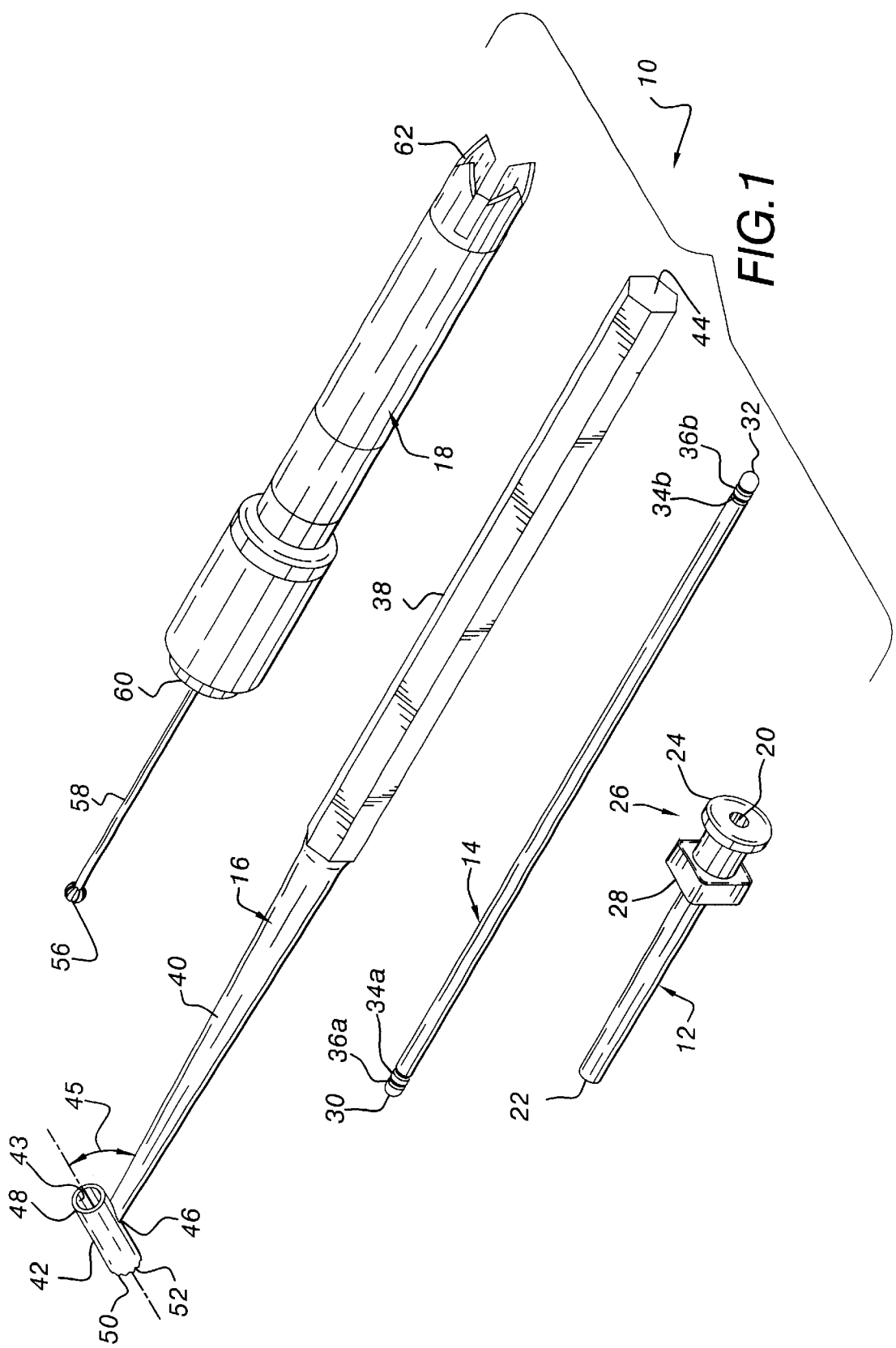

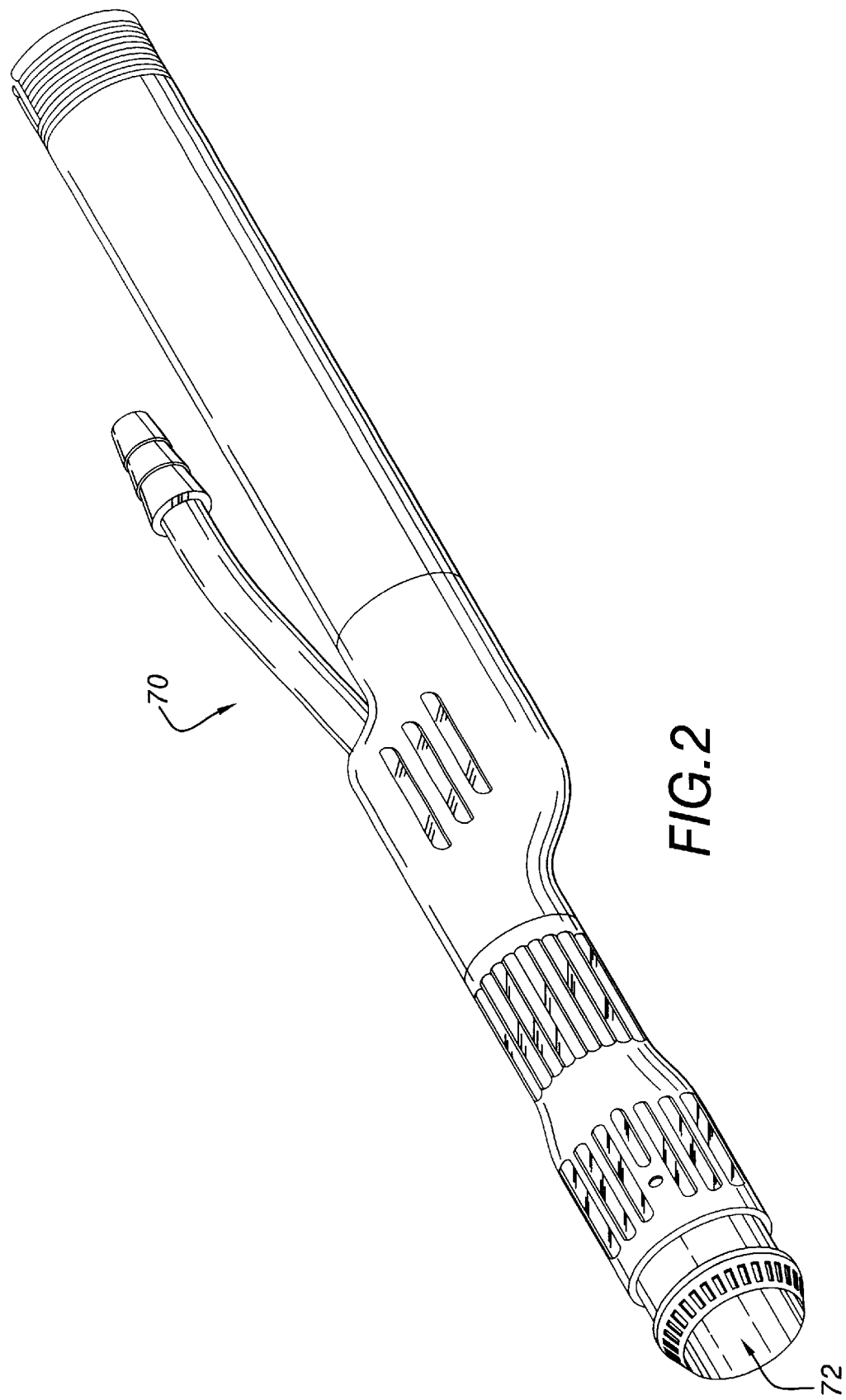

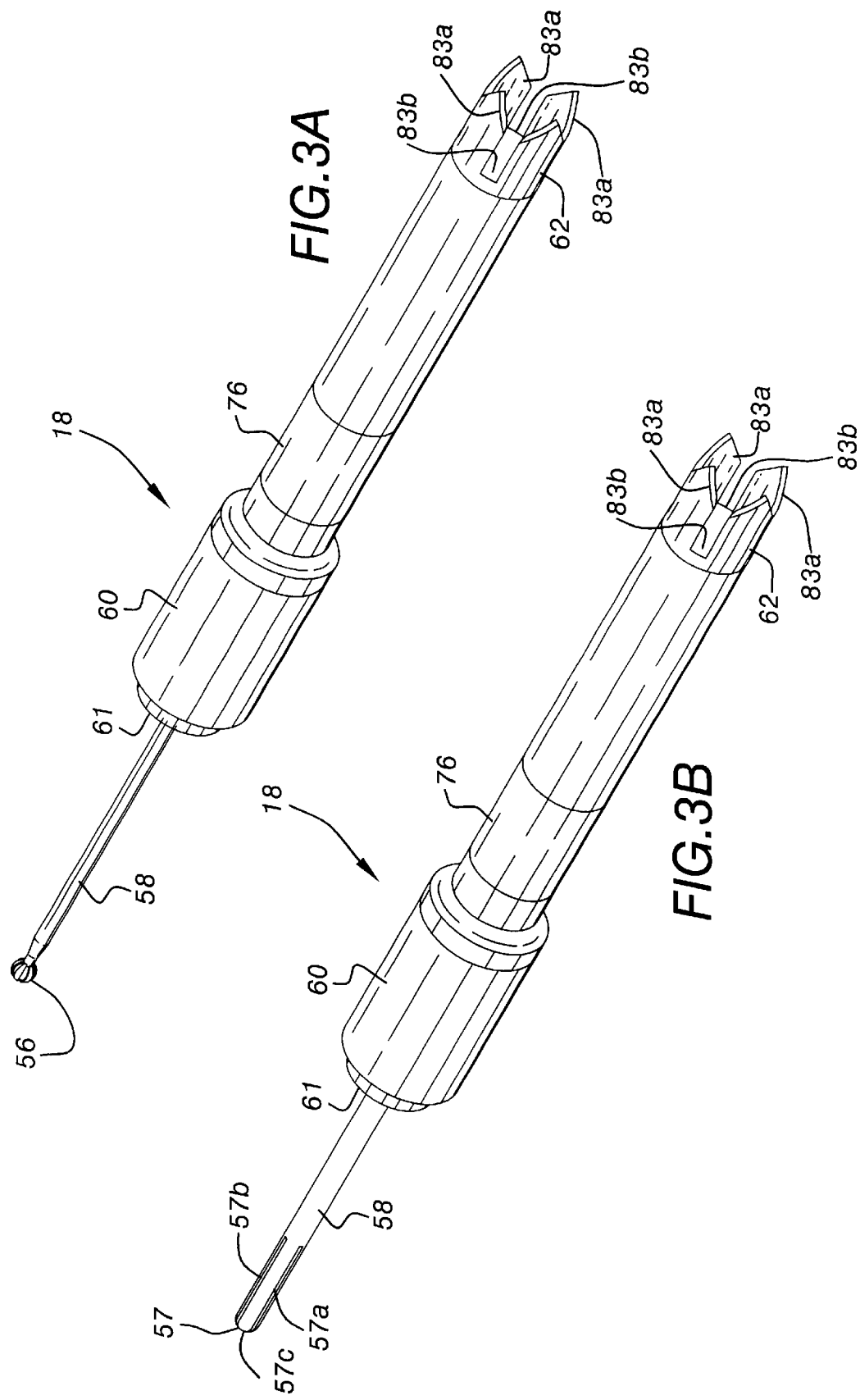

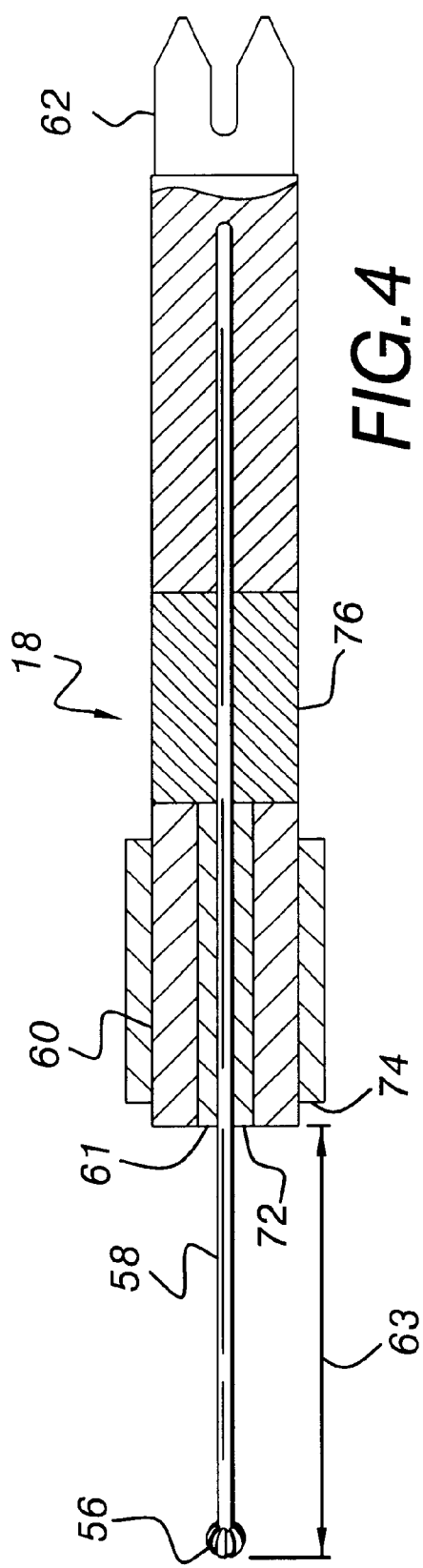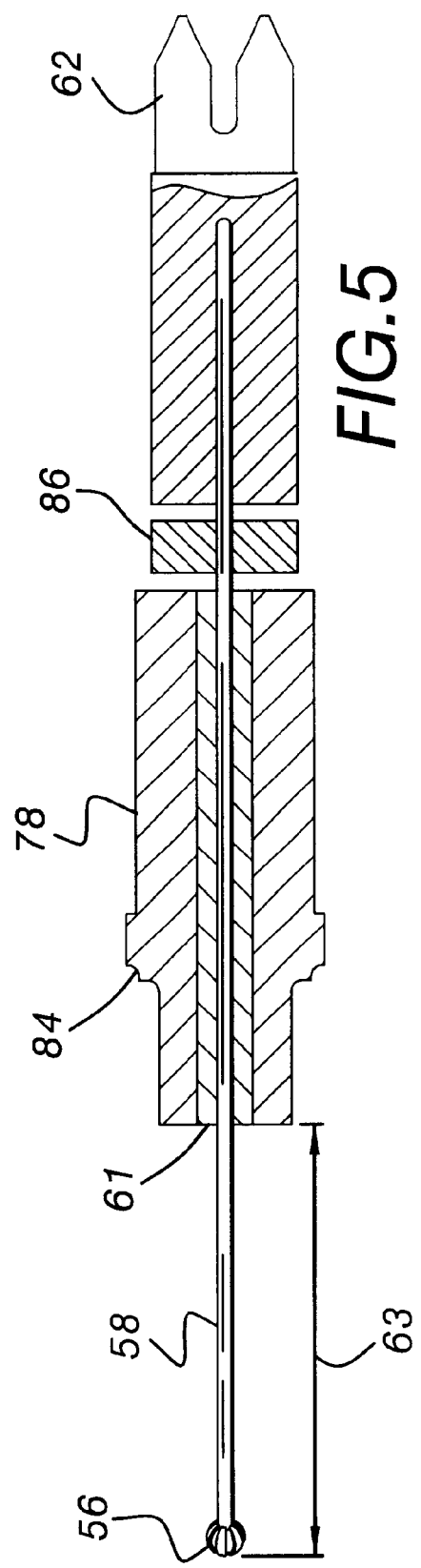

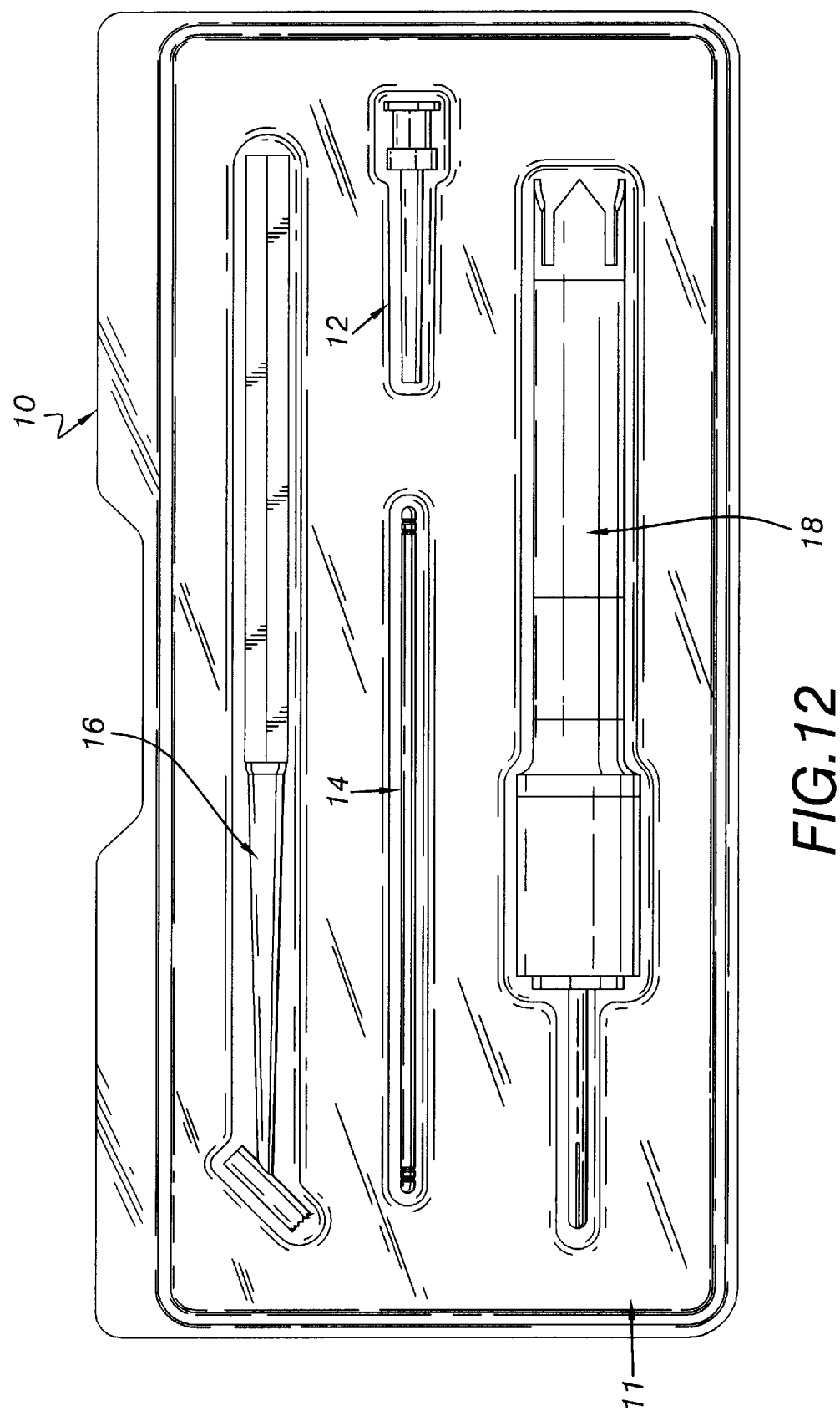

METHOD FOR PROTECTING SOFT TISSUE WHILE DRILLING INTO UNDERLYING BONE

This application is a divisional of U.S. patent application Ser. No. 09/305,342 filed Apr. 30, 1999, now U.S. Patent No. 6,238,400, issued May 29, 2001, which claims priority to U.S. provisional application Ser. No. 60/083,762, filed May 1, 1998, the entire disclosures of which are incorporated herein by reference.

BACKGROUND OF THE INVENTION

1. Field of the Invention

The present invention relates to a method and apparatus for trephination and irrigation of a cavity in the body, particularly the frontal sinus cavity.

2. Discussion of the Prior Art

In treatment of frontal sinus cavity disease, a hole or trephination is drilled in the sinus frontal bone, a needle is inserted through the hole into the frontal sinus cavity and the cavity is irrigated to relieve pain and flush out unwanted substances, such as purulent secretions contained within the cavity. The above procedure for flushing the frontal sinus cavity is referred to as trephination and irrigation of the frontal sinus cavity.

Some of the disadvantages of prior art procedures for trephination and irrigation of the frontal sinus cavity include difficulty in locating and maintaining the position of the trephination or hole after the trephine or drill is removed and associated time and trauma. More particularly, once the drill is removed, the small hole is often re-covered by the soft tissue or skin and an excessive amount of time is required to re-locate the hole, especially if the skin over the hole is loose or slack. Another disadvantage is that irrigation with a needle through the hole is complicated by irrigation fluid flowing back out of the hole around the needle. In the past, sealing around the needle has been attempted with finger pressure by pinching the needle proximate the hole in a largely unsuccessful attempt to stem a messy outflow resulting in possible fluid infiltration into the soft tissues around the eye.

Another procedure used in the prior art for trephination and irrigation of the frontal sinus cavity is frontal drill-out from the inside with a bur. The frontal drill-out procedure has the disadvantages of being technically challenging, difficult to perform with either manual or powered instruments (e.g., drills or shavers), and of destroying substantial tissue.

OBJECTS AND SUMMARY OF THE INVENTION

Accordingly, it is a primary object of the present invention to overcome the above-mentioned disadvantages associated with frontal sinus irrigation.

Another object of the present invention is locating and maintaining a trephine hole for accurate placement of an irrigation cannula in the frontal sinus cavity.

A further object of the present invention is to irrigate the frontal sinus through a trephine hole in the frontal bone without backflow through the hole by use of a sealing, tapered cannula.

A further object of the present invention is to use a soft tissue protective drill guide to drill a hole in bone in a manner to provide alignment for drilling and placement of an irrigating cannula.

The present invention has another object in a method of trephination and irrigation of the frontal sinus cavity in a safe and accurate manner with the use of a drill guide and a powered drill configured to prevent contact with the posterior wall of the frontal sinus cavity.

The aforesaid objects are achieved individually and in combination, and it is not intended that the present invention be construed as requiring two or more of the objects to be combined unless expressly required by the claims attached hereto.

In accordance with the present invention, a trephination and irrigation set or kit includes a drill guiding, soft tissue protector sleeve, a trephination instrument (e.g., drill or bur) having a length to extend a short distance beyond the protector sleeve when fully inserted, a guide pin or rod dimensioned to fit into the trephination or hole for locating and preserving the hole through the soft tissue defect or incision and a tapered, blunt irrigating cannula configured to sealingly lodge in the hole in the frontal bone for introducing irrigation fluid into the frontal sinus cavity.

In accordance with the method of the present invention, a trephination site is selected on the anterior front face of the frontal sinus, and an incision through the skin is made large enough to accept the tubular drill guide which is then inserted into the incision and depressed against the frontal bone of the skull, over the frontal sinus. The drill guide has teeth at its distal edge for securely gripping the bony surface. A trephine hole is drilled in the frontal bone by passing a trephination instrument through the lumen in the drill guide after which the trephination instrument is withdrawn from the drill guide. The guide pin is then inserted through the lumen of the drill guide and into the trephine hole, whereupon the drill guide is removed and the irrigation cannula is inserted over the guide pin and into the trephine hole. Irrigation fluid is then forced into the frontal sinus through the cannula.

The above and still further objects, features and advantages of the present invention will become apparent upon consideration of the following detailed description of a specific embodiment thereof, particularly when taken in conjunction with the accompanying drawings wherein like reference numerals in the various figures are utilized to designate like components.

BRIEF DESCRIPTION OF THE DRAWINGS

FIG. 1 is a plan view, in perspective, of a trephination set including (from left to right) an irrigation cannula, a guide pin, a guiding soft tissue protector sleeve and a trephination instrument for attachment to a powered handpiece.

FIG. 2 is a perspective view of a surgical handpiece adapted to receive a motor for driving the trephination instrument of FIG. 1.

FIGS. 3A and 3B are perspective views of a bur and a fluted drill, respectively, in accordance with the present invention.

FIG. 4 is a partial cross-section of the trephination instrument of FIG. 1.

FIG. 5 is a partial cross-section of an alternative embodiment of a trephination instrument, in accordance with the present invention.

FIG. 12 is a plane view of a trephination and irrigation kit according to the present invention.

DESCRIPTION OF THE PREFERRED EMBODIMENT

Figure 6:
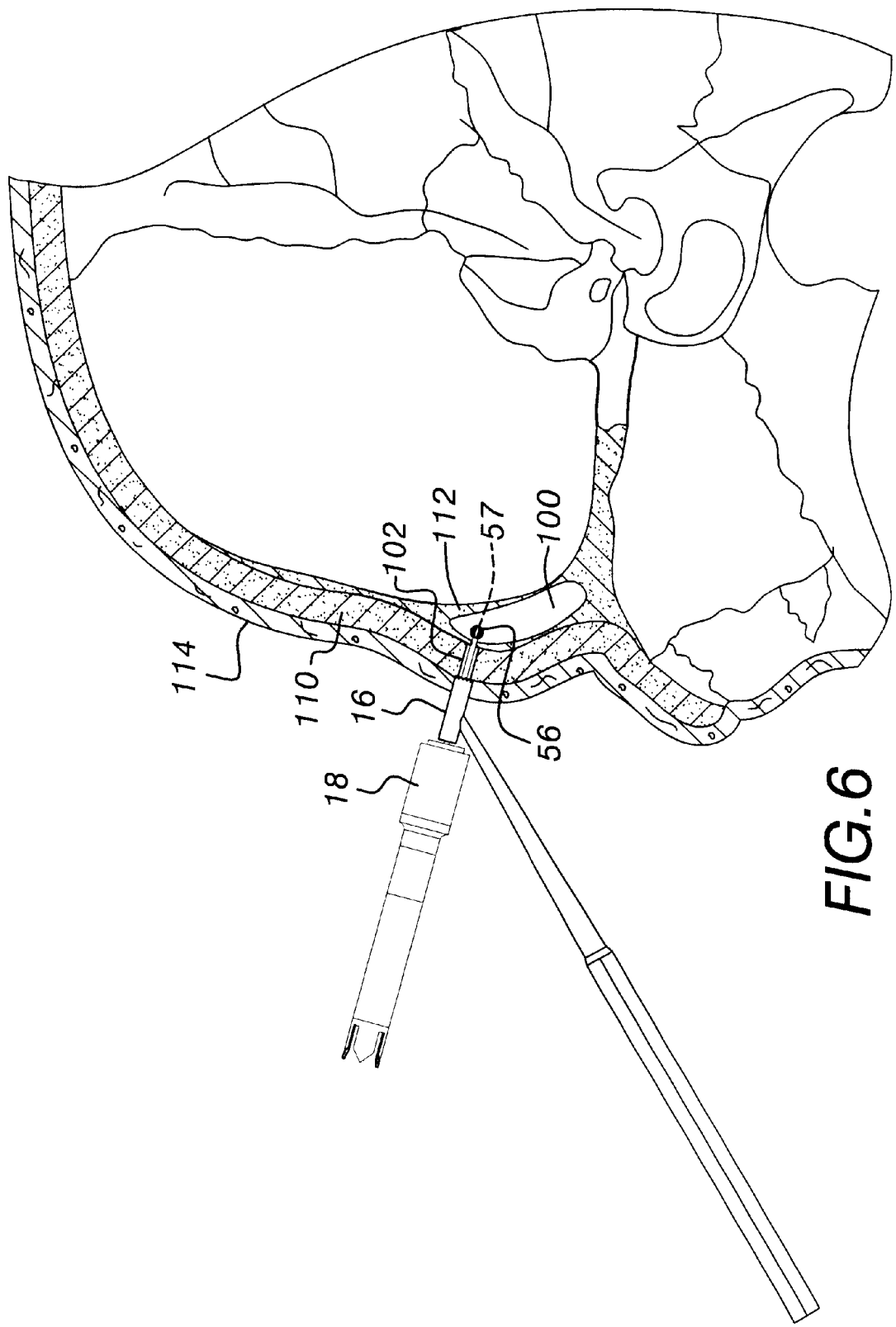
FIGS. 6, 7 and 8, are partial cross sections of the skull illustrating the method of the present invention.

In accordance with the present invention, a trephination and irrigation set 10 includes, as shown in FIG. 1, an irrigation cannula 12, a guide pin 14, a drill guide or guiding soft tissue protector sleeve 16 and trephination instrument 18 (e.g., a bur) for attachment to a powered handpiece. Cannula 12 is a tapered, elongate, rigid tube having a lumen 20 therethrough, and the cannula tapers to a narrower outside diameter (OD) toward a contoured, rounded or chamfered distal end 22. Cannula proximal end 24 preferably includes a standard Luer lock coupling 26 spaced from a medial flange 28.

Guide pin 14 is an elongate rigid rod, preferably of circular cross section with an OD sized to be received within lumen 20 of cannula 12 and protector sleeve 16. Guide pin 14 is terminated in first and second rounded ends 30, 32. Proximate each rounded end 30, 32, are located first and second grip control circumferential grooves 34a, 36a, 34b, 36b respectively; the outermost grip control grooves 36a, 36b are between and spaced from the inner grip control grooves 34a, 34b and the respective guide pin ends 31, 32. Grip control grooves 34a, 36a, 34b, 36b are preferably V-shaped and have a shallow depth.

Protector sleeve or drill guide 16 has a proximal handle 38 connected to a tapered segment 40 terminated distally in a connection to a tubular sleeve 42. Handle 38 is joined to tubular sleeve 42 at an angle 45 of approximately forty-five degrees (handle axis to tubular sleeve axis, as shown in FIG. 1) for convenient positioning of the sleeve. Tubular sleeve 42 is preferably an open ended cylinder with a lumen 43 having a predetermined length between a proximal open end 48 and a distal (or periosteal) open end 50 including a ring of sharp, bone gripping teeth or serrations 52. For purposes of nomenclature, distal open end 50 is defined as lying in a plane including the tips or ends of teeth or serrations 52. Protective sleeve lumen 43 is sized to receive both the trephination instrument 18 and the guide pin 14. The protective sleeve proximal open end 48 carries an abutment surface which serves to limit distal travel of the trephination instrument 18 when inserted in the protective sleeve.

Trephination instrument 18 (as shown in FIG. 1) can include either a bur 56 or drill 57, as illustrated in FIGS. 3A and 3B, respectively. The bur 56 or drill 57 is incorporated into the distal end of a stainless steel shaft 58 proximally received in a hub 60. The exposed length from the distal end of hub 60 to the distal end 57c of bur 56 or drill 57 has a selected length which is slightly longer than tubular sleeve 42. Trephination instrument 18 includes a distally facing abutment surface 61 (as best seen in FIGS. 3A, 3B, 4 and 5). Trephination instrument abutment surface 61 serves to limit distal travel of the trephination instrument 18 when inserted in the protective sleeve 42 by bearing against and abutting the protective sleeve abutment surface on the protective sleeve proximal end 48. The distance 63, shown in FIG. 5, between the trephination instrument distal end and the trephination instrument abutment surface 61 is greater than the length of tubular sleeve 42, which is the distance between the abutment surface on the proximal open end 48 and the distal open end 50.

Straight fluted drill 57, shown in FIG. 3B is a cutting tip or penetrating tool preferably having a two-flute rounded nose cutter with straight flutes and a rounded nose. First and second straight flutes 57a, 57b are terminated distally in rounded distal end 57c. The straight flutes provide a very similar feel to a bur but allow insertion of a continuous diameter drill into the drill guide 16, providing stability and avoiding having a bur hook on the underside of the inner surface of the bony wall after penetration. Drill 57, having straight flutes 57a, 57b, advances only when the surgeon applies pressure and does not "corkscrew" or advance merely due to drill shaft rotation, thus avoiding inadvertant contact with the brain.

For either embodiment of the trephination instrument 18 (e.g., drill 57 or bur 56), the distal end of the trephination instrument is inserted into protector sleeve 16 and has a length selected to permit the trephination instrument distal end to project distally beyond the distal end 50 of sleeve 16 (as shown in FIG. 6), extending a selected extension distance (preferably approximately seven mm) beyond sleeve distal end 50. The extension distance or distance which the bur or drill distal end projects beyond sleeve distal end 50 is selected to be less than the combined thickness of the skull front table and depth of the frontal sinus cavity, thereby preventing contact of the trephination instrument distal end (e.g. 57c) with the posterior sinus wall 112, as shown in FIG. 6, thus avoiding inadvertent contact with the brain.

Turning to FIGS. 3A and 4, hub 60 of instrument 18 includes a metal sleeve/bearing 72 through which shaft 58 passes internally and is proximally connected to and rotatably driven by proximal coupler 62. Hub 60 includes a distal annular notched shoulder 74 for detent engagement in a powered handpiece 70. A thrust bearing or washer 76 is slidably disposed between coupler 62 and hub 60 around shaft 58 and is fabricated from PTFE (e.g., Teflon® brand PTFE) or brass. An alternate embodiment is illustrated in FIG. 5, in which hub 78 includes a metal sleeve/bearing 80 through which shaft 58 passes internally and is proximally connected to and rotatably driven by proximal coupler 62. Proximal coupler 62 includes four prongs 83a radially arrayed and separated by four slots 83b arrayed at a uniform 90° spacing therebetween as shown in FIGS. 3A and 3B. Hub 78 includes a distal annular array of locking bumps interspersed with partial spherical recesses 84 for engagement in powered handpiece 70. A thrust bearing or washer 86 is slidably disposed between coupler 62 and hub 78 around shaft 58 and is preferably fabricated from PTFE or brass. The trephination instrument 18 is driven by a powered handpiece (e.g., a Xomed Surgical Products, Inc. StraightShot™ handpiece). FIG. 2 is a perspective view of a StraightShot™ powered surgical handpiece 70 adapted to receive a motor for driving a trephination instrument, (e.g., drill or bur). Handpiece 70 includes a distal receiving aperture 73 into which trephination instrument 18 is received.

Turning now to FIGS., 6, 7, 8 and 9, in a typical patient with sinus cavity disease, the frontal sinus cavity 100 is treated through a trephination or hole 102 drilled through the frontal bone front table 110. Preferably, CT scan measurements are taken of the anterior-to-posterior dimension of frontal sinus cavity 100 to determine the exact depth of the frontal sinus cavity. Knowing the exact depth of the frontal sinus cavity allows the surgeon to avoid penetrating the posterior wall 112 during drilling or trephination, it being noted that the bur or drill can be extended only a limited distance, thereby preventing contact with the posterior wall of the frontal sinus and possible contact with the brain.

Figure 7:
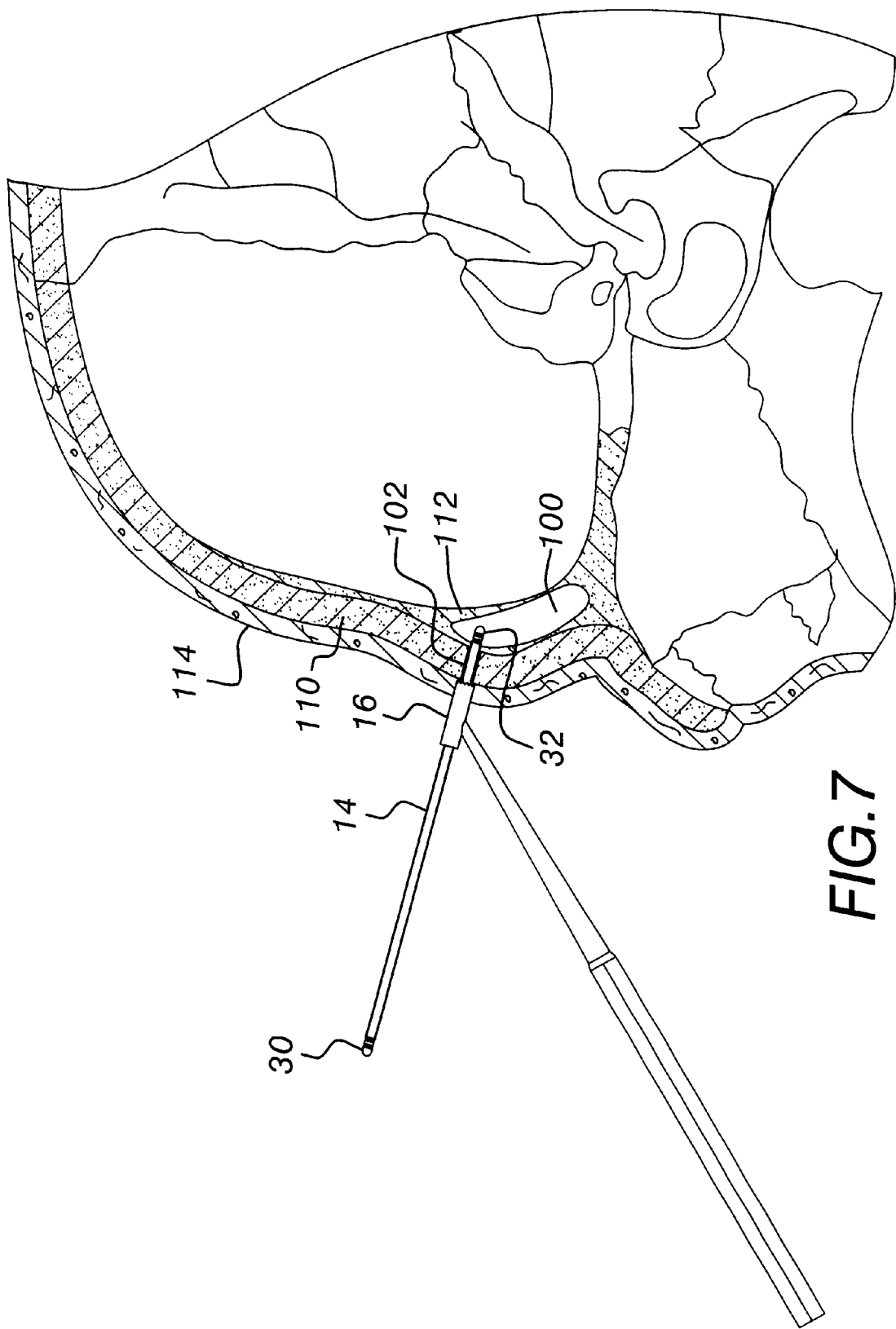
Figure 8:
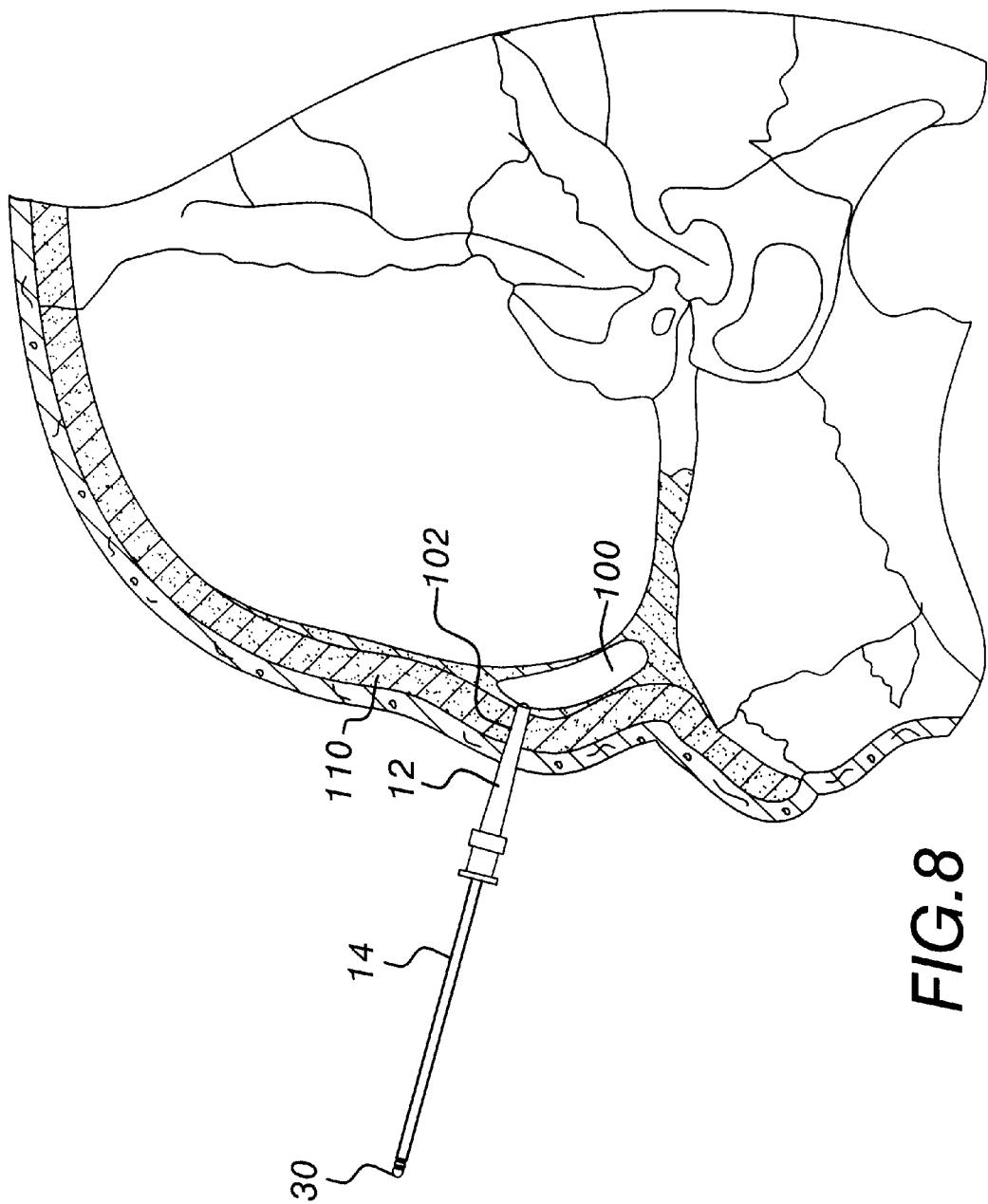

In practicing the method of the present invention, the patient's skin or soft tissue 114 may be prepped with an antiseptic (such as Betadine™), and the landmarks are palpated. The landmarks are preferably the supraorbital foramen notches (both sides), and a line is drawn across the landmarks. The trephination is to be along a line defined in the medial part of the brow to hide or camouflage the trephination site. Preferably, the trephination site is on the anterior front face of the frontal sinus to facilitate subsequent location and re-cannulation at the site. At the first trephination site, a small incision is made (e.g., with a scalpel) through the skin 114. The incision should be just large enough to accept the soft tissue protector sleeve or drill guide 16 which is then inserted into the incision and depressed against the bony surface of the skull as shown in FIG. 6. As noted above, drill guide 16 has teeth or serrations 52 at its periosteal (or distal) edge 50 and, when pressed against the bony surface of the front table 110, grips the bony surface securely. Trephination instrument 18 is inserted through the proximal open end 48 and into the lumen 43 of drill guide 16. As noted above, the length of trephination instrument shaft 58 is sized to penetrate a limited extension distance, approximately seven mm, past the drill guide distal end 50 with maximal entry of the bur element 56. The seven mm limited extension distance is selected to be smaller than the bone thickness plus the depth of the patient's frontal sinus cavity, thus allowing the surgeon to avoid penetration of the posterior wall 112. Next, without irrigation and at a fairly low trephine rate (e.g., drilling at 3000–6000 RPM), the bur or drill is placed through the drill guide 16 against the bony surface of front table 110, and powered handpiece 70 is turned on or actuated, drilling straight through front table 110. The surgeon preferably will elect to avoid a curved or concave trephine site because the bur element 56 may skate across a curved bony surface. Once the bur element 56 or drill tip is in the frontal sinus cavity 100, the guiding drill guide 16 is used to maintain the location of the trephine hole 102 while the trephination instrument is withdrawn whereupon the drill guide 16 remains in place, fixing the location of hole 102. As shown in FIG. 7, rounded end 32 of guide pin 14 is inserted into the drill guide 16 and projects into trephine hole 102. After guide pin 14 is inserted through the trephine hole 102 and projects into frontal sinus cavity 100, the surgeon axially withdraws the soft tissue protector 16 while leaving guide pin 14 in place in trephine hole 102 and, as shown in FIG. 8, cannula 12 is placed over exposed guide pin end 30 and guide pin 14 is used to axially guide cannula 12 as it is distally advanced into press-fit sealing engagement with the trephine hole 102, whereupon guide pin 14 is proximally, axially withdrawn providing a patent cannula lumen 20 in fluid communication with sinus cavity 100.

The tapered irrigation cannula 12 is configured and sized (in diameter and length) to be retained within the trephine hole 102 in the frontal sinus 100. Cannula 12 is configured to avoid falling into the sinus 100 and fits sealingly in the hole 102 created with the trephination instrument. The irrigation cannula is thereby lodged and securely anchored into the front face of the frontal bone 110 and preferably does not enter substantially into the sinus cavity 100.

Figure 9B:
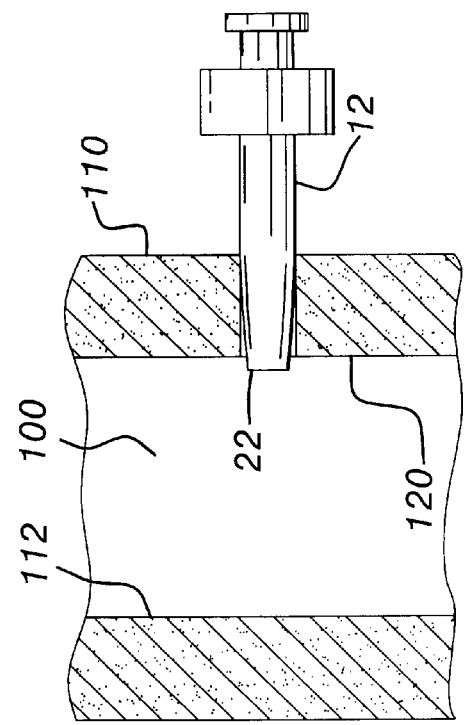
FIGS. 9a and 9b are diagrams illustrating cannula insertion through the front table, in accordance with the method of the present invention.
Figure 9A:
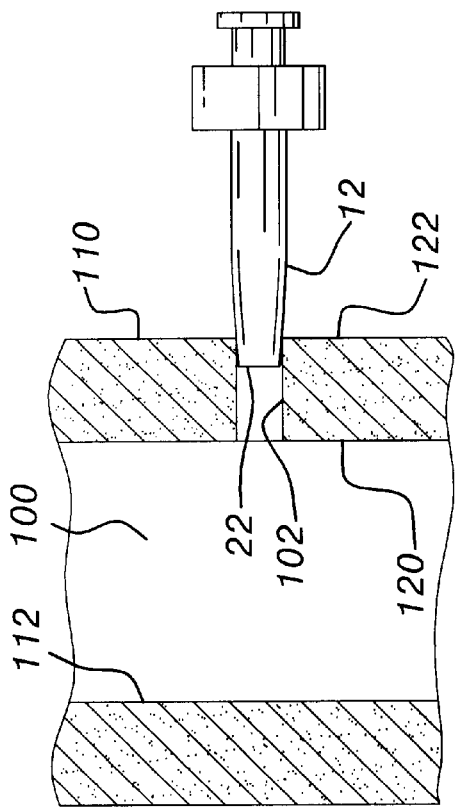

Turning now to the diagrams of FIGS. 9a and 9b, FIG. 9a shows a five mm thick front table (or frontal wall) with hole or trephination 102 drilled therethrough, and with a cannula 12 inserted therein. A two mm bur element 56 or drill 57 creates a 2.03 mm trephine hole 102 in the frontal wall. If the trephine hole 102 does not enlarge (upon insertion) due to bone compression, the cannula tip or distal end 22 does not protrude through or past the interior surface 120 of frontal wall 110. Instead, the cannula distal end 22 penetrates approximately one mm beyond the outer surface 122 of frontal wall 110. However, if trephine hole 102 is enlarged due to bone compression or compacting, the hole enlarges to approximately 2.28 mm diameter and cannula distal end 22 protrudes beyond interior surface 120 by about one mm, as shown in FIG. 9b. The tapered exterior profile of cannula 12 is matched to the diameter of trephination instrument (e.g., bur element 56 or drill 57) to provide a press-fit sealing engagement between cannula 12 and trephine hole 102, while preventing an over-insertion of the cannula into the frontal sinus. The sealing engagement between the cannula and the hole 102 permits irrigation fluid to be forced under pressure into the sinus cavity 100 without causing backflow through trephine hole 102.

Figure 10:
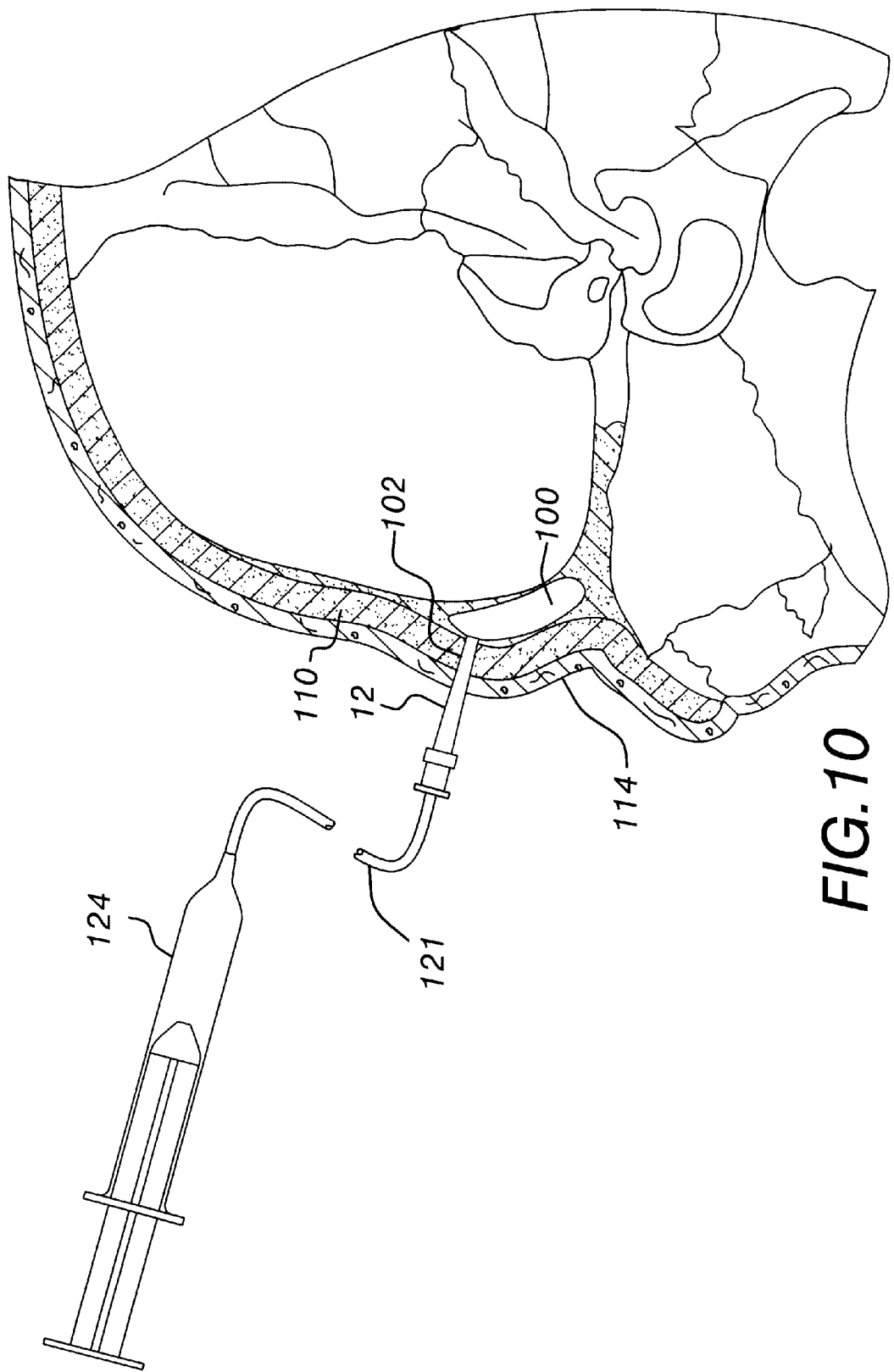
FIGS. 10 and 11 are partial cross sections of the skull illustrating the method of the present invention.
Figure 11:
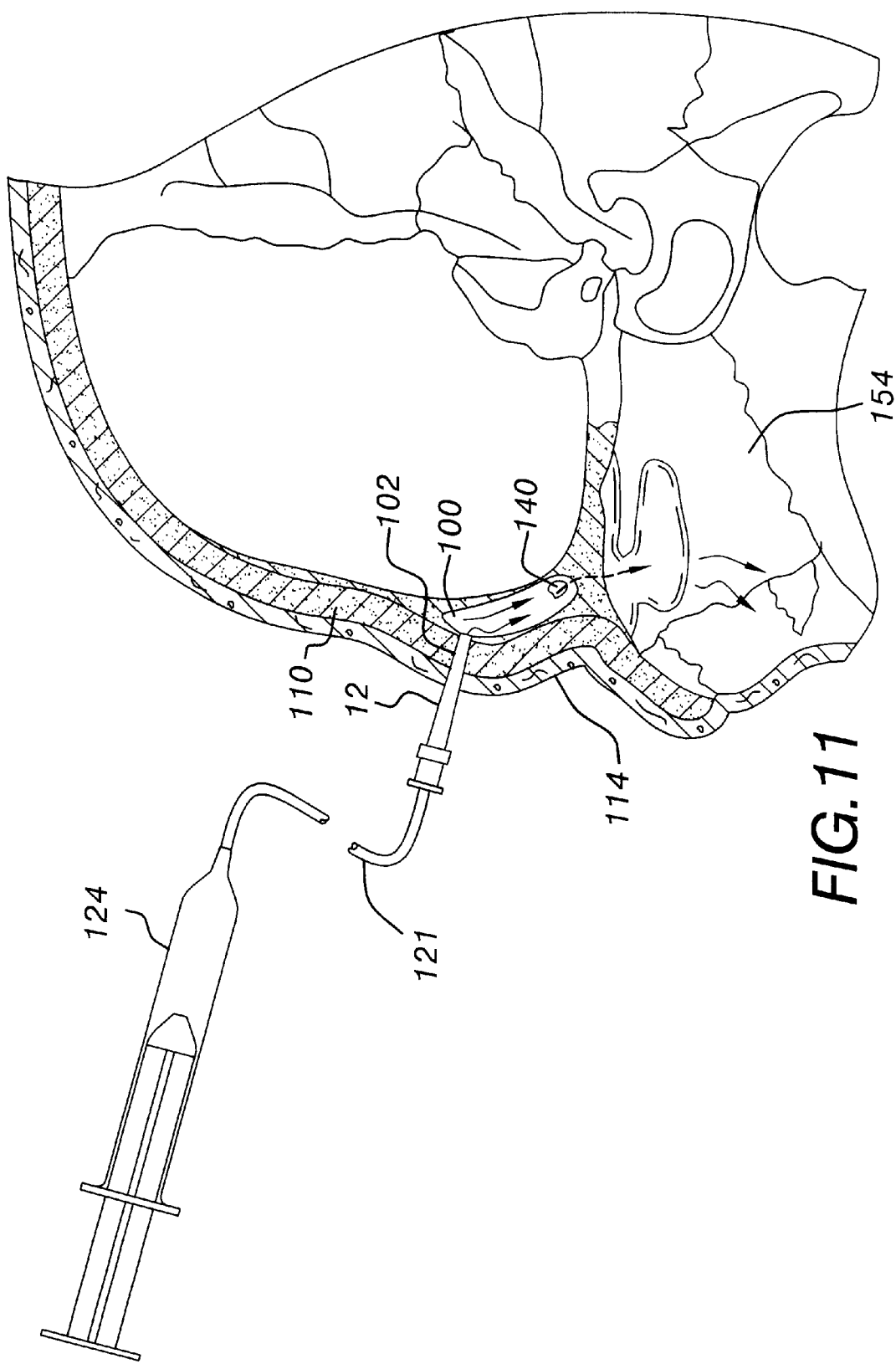

As shown in FIG. 10, standard I.V. irrigation tubing 121 is connected to the irrigation cannula proximal end 24. The I.V. tube 121 is also connected to a syringe 124 or other fluid source filled with fluid (e.g., saline) for irrigation or flushing of sinus cavity 100. The surgeon may ben draw back or aspirate to see either bubbles or pus come into irrigation tubing 121 before irrigating into cavity 100. Preferably, an endoscope (not shown) is inserted into the corresponding nostril (e.g., left nostril for left frontal sinus) to provide an endoscopic view and aspiration of effluvia. As best seen in FIG. 11, the flow of saline solution into frontal sinus cavity 100 is expelled into the nasal passage 154; as sinus cavity 100 is pressurized with the saline, purulent secretions are expelled through the nasofrontal duct 140 and are delivered into the nasal passage 154, without traumatizing the nasal frontal recess. To insure all secretions have been delivered into the nasal passage 154, irrigation is continued until a constant stream of clear irrigation fluid flows from the frontal sinus cavity 100, thereby indicating that the frontal sinus is completely cleared of foreign matter. The patient's second frontal sinus can then be cleared by repeating the procedure at a second trephination site selected from a position along the line defined in the medial part of the brow, as described above.

The method of the present invention relies on the apparatus described above to provide a safe trephination into the frontal sinus; more particularly, the method of drilling into a frontal sinus cavity having a depth defined between posterior wall 112 and frontal wall 110 having a thickness includes the steps of providing drill guide 16 having a distal end 50 for engaging frontal wall bone 110 and a proximal end 48 carrying an abutment surface with a predetermined distance between distal end 50 and proximal end 48. Instrument 18 has a distal end 57c and a proximal abutment surface 61 with a predetermined distance 63 therebetween. The extension distance, as described above, is less than the depth of the frontal sinus cavity 100 added to the thickness of the frontal bone 110 and greater than the thickness of the frontal bone 110, or approximately seven mm. Next, the surgeon places the distal end 50 of the drill guide in engagement with frontal bone 110 and drills a hole in the frontal bone by inserting the instrument 18 through drill guide 16. The distal drilling tip 57c is prevented from engaging the sinus cavity posterior wall 112 by engagement of the powered drill abutment surface 61 with the drill guide abutment surface on proximal end 48.

Trephination and irrigation set 10 is preferably packaged as a kit, shown in FIG. 12, including a package or housing 11 with recesses for cannula 12, guide pin 14, protector sleeve 16 and a trephination instrument 18.

In the preferred embodiment, cannula 12 is made of 300 series stainless steel and has a length (from distal end 22 to flange 28) of 0.875 inches; the OD of cannula 12 is 0.091 inches proximate medial flange 28, 0.083 inches at a distance of 0.118 inches from distal end 22 and tapers down to an OD of 0.076 inches at distal end 22. The inside diameter of lumen 20 is 0.061 inches. Cannula 12 is therefore tapered at an angle between approximately 0.2 degrees and 0.5 degrees. The sidewall of cannula 12 can be of uniform thickness or can vary in thickness.

Guide pin 14 is preferably made of 300 series stainless steel and preferably has an OD of 0.059 inches, a length of three inches and the outermost grip control grooves 36a, 36b are spaced one eighth inch from the inner grip control grooves 34a, 34b, which are located three eighths of an inch from the respective guide pin ends 31, 32. Grip control grooves 34a, 36a, 34b, 36b are preferably V-shaped and have a depth of 0.012 inches.

Protector sleeve or drill guide 16 is preferably made of 300 series stainless steel and proximal handle 38 has a hexagonal cross sectional shape connected to tapered segment 40 terminated distally in a connection to a tubular sleeve 42; the combined length of the handle 38 and tapered segment 40 is four and one-half inches from proximal end 44 to the tubular sleeve connection 46. Handle 38 and tapered segment 40 are coaxially aligned with one another and tapered segment 40 is welded or joined to tubular sleeve 42 at an angle 45 of forty-five degrees (handle axis to tubular sleeve axis, as shown in FIG. 1). Tubular sleeve lumen 43 is 0.083 inches (or 2.11 millimeters (mm)) in inner diameter (ID) and sleeve 42 has an OD of 0.109 inches. The preferred length of tubular sleeve 42 from proximal end 48 to opposing distal end 50 is 0.724 inches (i.e., 18.4 mm).

Trephination instrument 18 optionally includes a bur element 56 of two mm diameter affixed to the distal end of a stainless steel shaft 58. The 2 mm bur element 56 and shaft 58 together preferably have a combined, exposed length from the distal end of hub 60 to the distal end 57c of bur 56 of one inch (i.e., 25.4 mm).

Trephination, as used here, denotes either removal of a bone section or simple drilling or boring of a hole in a bony surface, preferably using a straight fluted drill, burr or the like; trephine, the verb, means creating a hole by boring, drilling or burring through a bony surface or the like. Drilling means trephining (e.g., as with a cylindrical saw), drilling with a drill-bit like surgical instrument, burring through (with a bur), or boring through a bony surface or the like. Bony surface, as used herein, means a surface including bone, cartilage, or other tissue or material through which a surgeon customarily drills or trephines. As noted above, a trephination instrument may be a drill, bur or trephine for use in the method of the present invention. Drill guide, guide tube and guide sleeve mean a structural member having a lumen therethrough sized to accept a drill, trephine or bur, and need not be, strictly speaking, a cylinder; the guide tube or sleeve can have any cross-sectional shape suitable to axially guide the drill or guide pin into a selected trephination or hole. The guide pin also need not be a rigid rod of circular cross section but can be any shape permitting insertion within a guide tube or which one may axially slide within a cannula.

As will be appreciated from the above, the method and apparatus of the present invention provide consistent and reliable trephination and cannula insertion for irrigation of the frontal sinus cavity utilizing a unique, self-aligning design. The drill guide with skin protector features an alignment guide for reliable insertion of the guide pin and irrigation cannula into the trephination hole, and the skin protection sleeve of the drill guide creates a safe barrier between the trephination instrument, such as a drill or burr, and surrounding soft tissues. The trephination instrument is designed for quick connection to a powered handpiece such as the STRAIGHTSHOT™ marketed by Xomed Surgical Products, Inc.; and the use of a straight-fluted drill creates a trephination hole while eliminating the need for additional drill/burr systems. The guide pin, after insertion through the drill guide into the trephination hole, provides positive alignment for the irrigation cannula. The tapered configuration of the irrigation cannula provides a press fit seal into the frontal sinus cavity bony structure to reduce external leaking of irrigation fluid during pressurized flushing of the frontal sinus.

In as much as the present invention is subject to various modifications and changes in detail, the above description of a preferred embodiment is intended to be exemplary only and not limiting. It is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A method for drilling and maintaining the location of a hole in bone covered by soft tissue, comprising the steps of:
   making an incision in the soft tissue;
   inserting a protector sleeve into the incision to engage the bone, the sleeve having a lumen therethrough;
   inserting a drill into the protector sleeve lumen;
   drilling into the bone to form a hole therein with the protector sleeve protecting the soft tissue from the drill;
   withdrawing the drill from the protector sleeve lumen; and
   inserting a pin into the protector sleeve lumen and into the hole.

2. A method for maintaining the location of a trephination hole, comprising:
   making an incision in the skin overlying bone;
   inserting a protector sleeve into the incision;
   inserting a drill into a lumen of the protector sleeve;
   drilling through the bone via the protector sleeve to make a trephination hole in communication with an anatomical cavity beneath the bone;
   withdrawing the drill from the protector sleeve lumen, leaving the protector sleeve in place to maintain the location of the trephination hole; and
   inserting a pin into the protector sleeve lumen and into the trephination hole.

3. A method for maintaining the location of a trephination hole, comprising:
   making an incision in the skin;
   inserting a protector sleeve into the incision;
   inserting a drill into a lumen of the protector sleeve;
   drilling into the body through the protector sleeve, thereby making a trephination hole;
   withdrawing the drill from the protector sleeve lumen; and
   inserting a pin into the protector sleeve lumen and into the trephination hole.

4. A method of claim 3, further comprising:
   withdrawing the protector sleeve while leaving the pin in the trephination hole.

* * * * *